United States Patent [19]

Ikeda et al.

[11] 4,448,769

[45] May 15, 1984

[54] ESTER OF 1,1-DIOXOPENICILLANIC ACID, AND USE THEREOF AS β-LACTAMASE INHIBITOR

[75] Inventors: Shoji Ikeda, Ibaraki; Fumio Sakamoto, Osaka; Goro Tsukamoto, Toyonaka; Shigeru Yamabe, Kobe, all of Japan

[73] Assignee: Kanebo Ltd., Tokyo, Japan

[21] Appl. No.: 396,471

[22] Filed: Jul. 8, 1982

[30] Foreign Application Priority Data

Jul. 15, 1981 [JP] Japan .................................. 56-109275
Oct. 23, 1981 [JP] Japan .................................. 56-168605

[51] Int. Cl.$^3$ .................. C07D 499/00; A61K 31/425
[52] U.S. Cl. ...................................... 424/114; 424/270; 260/245.2 R
[58] Field of Search ................. 260/245.2 R; 424/270, 424/114

[56] References Cited

U.S. PATENT DOCUMENTS 4,241,050 12/1980 Barth .......................... 260/245.2 R

FOREIGN PATENT DOCUMENTS 2000138A 1/1979 United Kingdom .

OTHER PUBLICATIONS

*Antimicrobial Agents and Chemotherapy*, 1978, pp. 414–419, American Society for Microbiology.
*Current Chemotherapy and Infectious Disease*, 1980, p. 353, American Society for Microbiology.

*Primary Examiner*—Nicholas S. Rizzo
*Attorney, Agent, or Firm*—Wenderoth, Lind & Ponack

[57] ABSTRACT

A 1,1-dioxopenicillanic acid ester represented by formula (I)

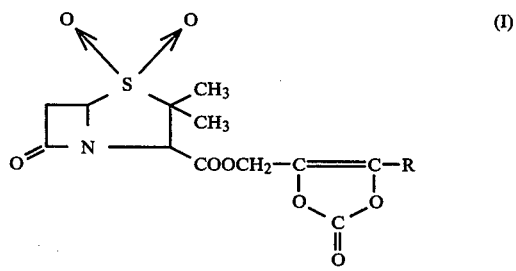

wherein R represents a methyl or phenyl group. The ester of formula (I) may be prepared by reacting 1,1-dioxopenicillanic acid or its salt with a compound represented by formula (III)

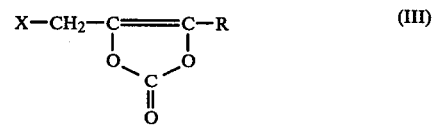

wherein R is as defined above, and X represents a halogen atom, or by oxidizing a compound of formula (V)

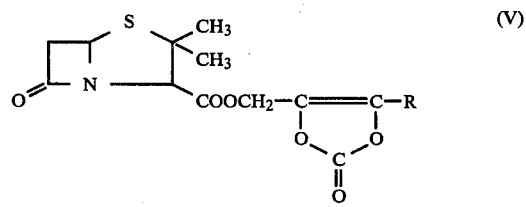

wherein R is as defined above. The ester of the formula (I) is useful as a β-lactamase inhibitor and may be used in association with a β-lactam antibiotic.

6 Claims, No Drawings

ESTER OF 1,1-DIOXOPENICILLANIC ACID, AND USE THEREOF AS β-LACTAMASE INHIBITOR

This invention relates to a novel ester of 1,1-dioxopenicillanic acid, a process for its production, and to its use as a β-lactamase inhibitor.

More specifically, this invention pertains to 1,1-dioxopenicillanic acid [5-methyl-(or phenyl)-2-oxo-1,3-dioxolen-4-yl]methyl ester represented by the following formula (I)

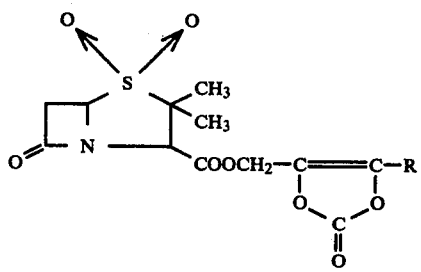

wherein R is a methyl or phenyl group; a process for its production; and its use as a β-lactamase inhibitor.

β-Lactam antibiotics are by far the most widely used antibiotics. Recently, however, the problem of microorganisms which have gained resistance to these antibiotics has come to the fore. It is known that the resistance of pathogenic microorganisms to β-lactam antibiotics is due mainly to the deactivation of the β-lactam antibiotics by β-lactamase produced by these microorganisms. Thus, the deactivation of β-lactam antibiotics can be prevented by using them in combination with β-lactamase inhibitors, and even when a β-lactam antibiotic alone has a low efficacy, the combined use of it with a β-lactamase inhibitor can expectedly produce the desired therapeutic effect.

From this viewpoint, some compounds have previously been proposed.

For example, British patent application No. 2000138A (1979) and Antimicrobial Agents and Chemotherapy, pages 414–419 (1978) disclose 1,1-dioxopenicillanic acid of the following formula (II)

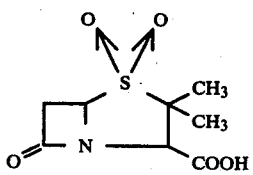

nd its esters of the following formula (II')

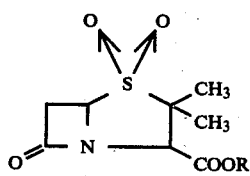

wherein R⁴ is alkanoyloxymethyl having from 3 to carbon atoms, 1-(alkanoyloxy)ethyl having from 4 to carbon atoms, alkoxycarbonyloxymethyl having from to 6 carbon atoms, 1-(alkoxycarbonyloxy)ethyl having from 4 to 7 carbon atoms, 3-phthalidyl, 4-crotonolactonyl, or γ-butyrolacton-4-yl, as β-lactamase inhibitors.

Current Chemotherapy and Infectious Disease, Vol. 1, page 353 [published by the American Society for Microbiology (1980)] discloses 1,1-dioxopenicillanic acid pivaloyloxymethyl ester of the following formula (II")

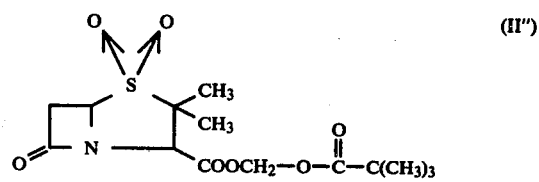

which is a typical compound falling within the aforesaid esters of formula (II'), as a prodrug for 1,1-dioxopenicillanic acid (II).

The present inventors made various investigations in order to obtain novel β-lactamase inhibitors which are better than the above-mentioned known compounds. These investigations have led to the determination that the novel esters of 1,1-dioxopenicillanic acid represented by formula (I) are excellent prodrugs for 1,1dioxopenicillanic acid (II).

It is an object of this invention therefore to provide a novel ester of 1,1-dioxopenicillanic acid.

Another object of this invention is to provide a novel ester of 1,1-dioxopenicillanic acid as an excellent β-lactamase inhibitor.

Still another object of this invention is to provide a pharmaceutical composition comprising the novel ester of 1,1-dioxopenicillanic acid and a β-lactam antibiotic.

A further object of this invention is to provide a suitable process for producing the novel ester of 1,1-dioxopenicillanic acid.

Other objects and advantages of this invention will become apparent from the following description.

In accordance with this invention, these objects and advantages are achieved firstly by a novel ester of 1,1-dioxopenicillanic acid represented by the following formula (I)

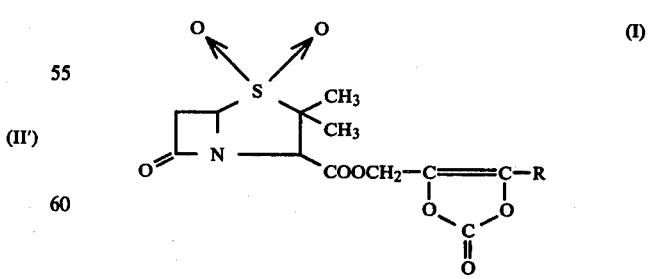

wherein R is a methyl or phenyl group.

The ester of formula (I) is either 1,1-dioxopenicillanic acid (5-methyl-2-oxo-1,3-dioxolen-4-yl)methyl ester of the following formula (I-A)

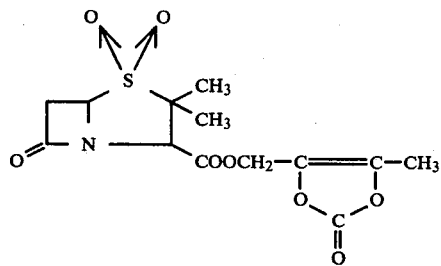

(I-A)

or 1,1-dioxopenicillanic acid (5-phenyl-2-oxo-1,3-diox-olen-4-yl)-methyl ester of the following formula (I-B)

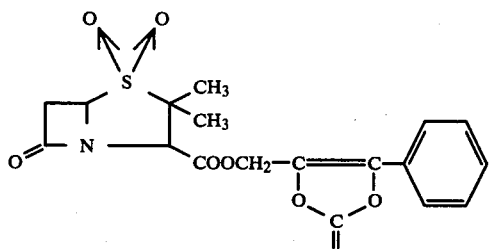

(I-B)

depending upon the definition of R in formula (I).

The compound of formula (I) in accordance with this invention can be produced by method A or B below which is provided as the process of this invention.

Method A

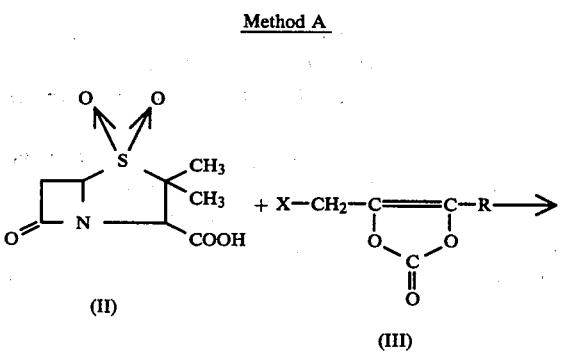

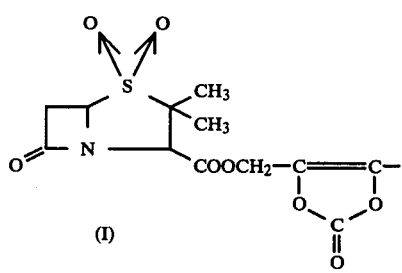

[R in formulae (I) and (III) is as defined above, and X in formula (III) is a halogen atom.]

Method B

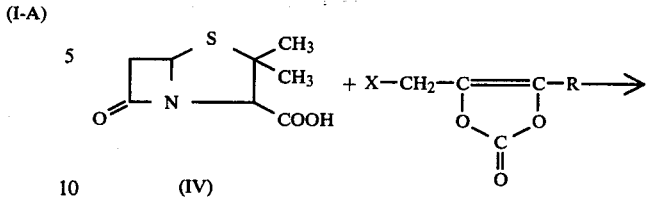

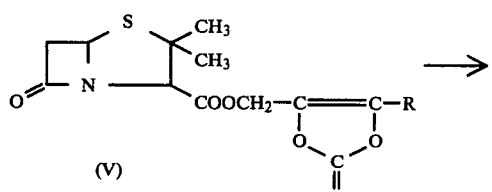

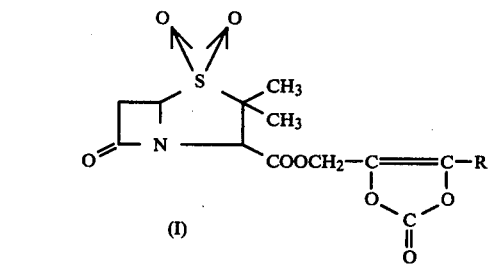

[R in formulae (I), (III) and (V), and X in formula (III) are as defined above.]

In the method A in accordance with this invention, 1,1-dioxopenicillanic acid or its salt as one material is a known compound, and can be produced by oxidizing penicillanic acid with potassium permanganate, a peroxy-carboxylic acid, etc. [British patent application No. 2000138A (1978)].

The other material, the 4-halomethyl-5-methyl (or phenyl)-1,3-dioxolen-2-one of formula (III), can be produced by the action of a halogenating agent on known 5-methyl(or phenyl)-1,3-dioxolen-2-one of the following formula (III')

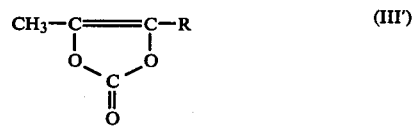

wherein R is as defined above [Tetrahedron Letters, pages 1071–1074 (1972); and Liebigs Annalen der Chemie, 764, pages 116–124 (1972)]. Examples of suitable halogenating agents for use in this reaction are N-bromo(or chloro)succinimide, N-bromo(or chloro)phthalimide, bromine and chlorine. In order to perform the halogenation reaction favorably, 1 mole or slightly over 1 mole, per mole of the compound (III'), of the halogenating agent is used, and reacted with the compound (III') in an inert solvent such as methylene chloride, carbon tetrachloride or benzene at room temperature to the boiling point of the solvent. Preferably, a radical initiator such as α,α'-azobisisobutyronitrile is used, or radicals are generated by ultraviolet irradiation. As a result, a compound of formula (III) in which X is chlorine or bromine is obtained. A compound of formula (III) in which X is an iodine atom can be produced by a known halogen-substitution reaction by, for example, reacting a compound of formula (III) in which X is a bromine atom with sodium iodide.

Preferably, the compound of formula (III) in which X is a bromine atom is used in the process of this invention.

The reaction of 1,1-dioxopenicillanic acid (II) or its salt with the compound (III) is carried out by using an equimolar proportion or a slightly excessive molar proportion of the compound (III) in the presence of a base, preferably in an inert organic solvent.

Preferably, an aprotic inert organic solvent, such as dimethylformamide, dimethyl sulfoxide, ethyl acetate and acetone, is used as the inert organic solvent, and examples of preferred bases are alkali metal hydrogen carbonates such as sodium hydrogen carbonate or potassium hydrogen carbonate, alkali metal carbonates such as sodium carbonate and potassium carbonate, and tertiary amines such as triethylamine.

The reaction is usually carried out at a temperature of $-40°$ to $80°$ C., preferably at $-10°$ C. to room temperature. The reaction can be completed in about 1 to 15 hours, usually in about 2 to 5 hours.

According to the method B in accordance with this invention, known penicillanic acid (IV) or its salt is reacted with the 4-halomethyl-5-methyl (or phenyl)-1,3-dioxolen-2-one (III) to form the penicillanic acid ester (V).

This reaction can be carried out under the same reaction conditions as in the reaction of 1,1-dioxopenicillanic acid (II) or its salt with the compound (III) in the method A.

Thereafter, the resulting penicillanic acid ester (V) is oxidized to give the desired 1,1-dioxopenicillanic acid ester (I).

In the oxidizing reaction, a peroxy-carboxylic acid such as peracetic acid or m-chloroperbenzoic acid is preferably used as an oxidizing agent. Hydrogen peroxide can also be used as a preferred oxidizing agent in the presence of a catalyst, for example an oxy acid of a heavy metal such as tungstic acid or molybdic acid or its salt, especially tungstic acid or its salt.

The peroxy-carboxylic acid is used in an amount stoichiometrically required to produce the dioxide (I) of the penicillanic acid ester (V) or in an amount exceeding it. Preferably, it is used in an amount of about 2 to about 2.2 moles per mole of the compound (V). Dichloromethane, chloroform, 1,2-dichloroethane, tetrahydrofuran, dioxane, ethyl acetate, etc. are preferably used as a reaction solvent. The reaction is carried out for 2 to 16 hours at a temperature of $-30°$ to $50°$ C., preferably $10°$ to $30°$ C.

Hydrogen peroxide is used in the presence of the aforesaid catalyst. It is used in an amount stoichiometrically required to produce the dioxide (I) of the penicillanic acid ester (V) or in an amount exceeding it. Preferably, its amount is about 2 to about 5 moles per mole of the compound (V). Dichloromethane, ethanol, isopropanol, tetrahydrofuran, etc. are used as a reaction solvent. The reaction is carried out at $-30°$ to $50°$ C., preferably $10°$ to $30°$ C. Usually, the reaction is performed for 24 to 48 hours. By using a catalytic amount of the aforesaid catalyst, the formation of the corresponding monoxide as a by-product can be inhibited, and the dioxide (I) can be obtained in a high yield.

The novel esters (I) of this invention are excellent prodrugs for 1,1-dioxopenicillanic acid (II), and are useful for the treatment of infectious diseases as $\beta$-lactamase inhibitors taken in combination with $\beta$-lactam antibiotics. This can be confirmed by the following experiments.

Test compounds used 1. 1,1-Dioxopenicillanic acid (5-methyl-2-oxo-1,3-dioxolen-4-yl)methyl ester [compound I-A of this invention]
2. 1,1-Dioxopenicillanic acid (5-phenyl-2-oxo-1,3-dioxolen-4-yl)methyl ester [compound I-B of this invention]
3. 1,1-Dioxopenicillanic acid pivaloyloxymethyl ester [control, the known compound (II″) shown hereinabove]
4. 1,1-Dioxopenicillanic acid [control, the known compound (II) shown hereinabove]

Test Example 1

Stability in an acidic medium (corresponding to artificial gastric juice):
(a) Test compounds
  Compound I-A and compound I-B were used.
(b) Test solution
  To 4.87 ml of the artificial gastric juice (pH about 1.2) described in The Pharmacopoeia of Japan, 10th edition was added 0.125 ml of a dimethyl sulfoxide solution of each of the test compounds (2 mg/ml). The solution was maintained at $37°$ C., and bioautography was performed as shown below after the lapse of 20 minutes, 40 minutes, and 60 minutes, respectively.
(c) Bioautography
  (i) The test solution was spotted on a TLC plate made by Merck & Co. (TLC plate Silicagel, $60F_{254}$, No. 5715), and developed with a mixture of chloroform and methanol (10:1 by volume).
  (ii) 0.1 ml of an aqueous solution of penicillin G potassium ($3.12 \times 10^3$ U/ml) and 0.2 ml of a suspension ($10^9$/ml) of Staphylococcus aureus 209P (11D 671) were added to 5 ml of an ordinary nutrient agar medium at about $40°$ C. Then, 0.1 ml of an aqueous solution of penicillinase ($200 \times 10^3$ U/ml; a product of Tokyo Kasei Kabushiki Kaisha) was added. The mixture was poured into a Petri dish, and cooled to prepare an assay agar medium for bioautography.
  (iii) The TLC plate obtained in (i) above was kept in intimate contact with the assay agar medium prepared in (ii) above for 30 minutes, and then the plate was removed. The agar medium was maintained at $4°$ C. for 60 minutes. The serum of a mouse was sprayed onto the medium, and the microorganism was cultivated overnight at $37°$ C.

The position (Rf value) of a growth inhibitory circular zone against Staphylococcus aureus on the above agar medium was determined.

According to the results of preliminary tests conducted under the conditions shown in (i), (ii) and (iii), compound I-A, compound I-B, and compound II had an Rf value of 0.67, 0.83, and 0.04, respectively.
(d) Results As a result of the above bioautography, with any of the solutions of compound I-A after standing for 20, 40 and 60 minutes, a growth inhibitory zone was observed at an Rf of 0.67 (compound I-A), and not at an Rf of 0.04 (compound II). With any of the test solutions of compound I-B, a growth inhibitory zone was observed only at an Rf of 0.83 (compound I-B) and not at an Rf of 0.04 (compound II).

Test Example 2

Stability in a basic medium (corresponding to artificial intestinal juice):

(a) Test compounds

Compounds I-A and I-B were used (b) Test solution

Test solutions for bioautography were prepared in the same way as in Test Example 1, (b) except that the artificial intestinal juice (pH about 6.8) described in The Pharmacopoeia of Japan, 10th edition was used instead of the artificial gastric juice.

(c) Bioautography

Bioautography was performed in the same way as in Test Example 1, (c).

(d) Results

With compound I-A, the same results as in Test Example 1 were obtained.

As regards compound I-B, a bacterial growth inhibitory zone was observed at an Rf of 0.83 (compound I-B) when the test solutions left to stand for 20 minutes and 40 minutes were tested. No growth inhibitory zone was observed at an Rf of 0.04 (compound II).

With the test solution left to stand for 60 minutes, bacterial growth inhibitory circular zones were observed not only at an Rf of 0.83 (compound I-B) but also at an Rf of 0.04 (compound II).

Test Example 3

Stability in mouse serum:

(a) Test compounds

Compounds I-A and I-B were used.

(b) Test solution 4 ml of mouse serum was added to 6 ml of 0.1 M phosphate buffer, and 0.2 ml of a solution prepared by dissolving 2 mg of each of the test compounds in 1 ml of dimethyl sulfoxide was added. The resulting solution was maintained at 37° C. for 10 minutes to form a test solution.

(c) Bioautography

It was carried out in the same way as in Test Example 1, (c) using the test solution obtained in (b) above.

(d) Results

With both compounds I-A and I-B, a bacterial growth inhibitory circular zone was observed only at an Rf of 0.04 (compound II), and no inhibitory circular zone was noted either at an Rf of 0.67 (compound I-A) or at an Rf of 0.83 (compound I-B).

Test Example 4

$\beta$-Lactamase inhibitory activity in mouse serum determined by oral administration:

(a) Test compounds

Compounds I-A, I-B, II″ (control) and II (control) were used.

(b) Administration

Each of the test compounds was dissolved in a 0.5% aqueous solution of carboxymethyl cellulose to prepare a solution having a concentration of 12 mg/ml.

The solution was orally administered to mice fasted for 16 hours (ddY-strain, male, 6 weeks old, body weight 25–30 g; five per group). The dose of each test compound was adjusted to 100 mg/kg of body weight calculated as the compound II.

(c) Test solution

After the lapse of 30, 60, 90 and 120 minutes from the administration of the test compound, blood was drawn from each of the mice in a group. The blood samples were each centrifuged at 3,000 rpm for 15 minutes to obtain serum samples. Serum samples obtained at the same blood drawing time were combined (each in an amount of 0.2 ml; total 1 ml) to form a test solution for each test compound.

(d) Measurement of $\beta$-lactamase inhibitory activity (the concentration of compound II in the blood)

The test solution obtained in (c) above was infiltrated into a paper disk (a thick disk having a diameter of 8 mm; a product of Toyo Roshi Kabushiki Kaisha). The paper disk (n=4) was then placed on an assay agar medium prepared in the same way as in Test Example 1, (c), (ii), and the microorganism was cultivated at 37° C. for 18 hours. The diameter of each bacterial growth inhibitory circular zone (mm, average of n=4) was measured.

(e) Results (i) The diameters of bacterial growth inhibitory circular zones in the test compounds were as shown in Table 1.

TABLE 1

| | Diameter of a bacterial growth inhibitory circular zone (mm) | | | |
|---|---|---|---|---|
| | Time elapsed after the administration (minutes) | | | |
| Compound | 30 | 60 | 90 | 120 |
| I-A | 37.5 | 33.5 | 32.8 | 30.8 |
| I-B | 33.3 | 31.6 | 30.5 | 29.3 |
| II″ (control) | 32.4 | 30.6 | 29.2 | 28.4 |
| II (control) | 30.9 | 29.4 | 26.0 | 22.9 |

(ii) From the diameters of the inhibitory zones shown in Table 1, the concentration of compound II (parent compound) in the blood at the time of administering each of the test compounds was determined. Specifically, by using the compound II, a calibration curve was prepared in accordance with the method described in (d) above regarding the concentration ($\mu$g/ml) of compound II and the diameter (mm) of a bacterial inhibitory circular zone. By using this calibration curve, the concentration of compound II in the blood at the time of administering each of the test compounds was determined. The results are shown in Table 2.

TABLE 2

| | Concentration of compound (II) in the blood ($\mu$g/ml) | | | |
|---|---|---|---|---|
| | Time elapsed after the administration (minutes) | | | |
| Compound | 30 | 60 | 90 | 120 |
| I-A | 39 | 21 | 19 | 14 |
| I-B | 20 | 16 | 14 | 12 |
| II″ | 18 | 14 | 11 | 10 |
| II | 14 | 12 | 6.8 | 4.3 |

Test Example 5

Acute toxicity:

The acute toxicities of compounds I-A and I-B were examined using ddY-strain male mice having a body weight of 25 to 30 g.

Both in oral and intraperitoneal administrations, the two compounds were found to have an $LD_{50}$ value of at least 1,000 mg/kg, and therefore had very low toxicity.

The results in Test Examples 1 and 2 show that the compounds I-A and I-B of this invention have high stability in artificial gastric juice and artificial intestinal juice. The results of Test Example 3 demonstrate that the compounds of this invention are decomposed rapidly (within 10 minutes) in the serum to form compound II (parent compound). Accordingly, the compounds I-A and I-B of the invention can be expected to be used as prodrugs for compound II (parent compound).

In fact, the results of Test Example 4 demonstrate that when compounds I-A and I-B are orally administered, they are easily absorbed, and a high level of the concentration of the compound II (parent compound) is developed rapidly and maintained in the blood for an extended period of time. They also show strong β-lactamase inhibitory activity.

The compounds I-A and I-B have extremely low toxicity as shown by the results of Test Example 5.

Accordingly, the compounds I-A and I-B of this invention are useful as excellent prodrugs for compound II (parent compound).

According to this invention, therefore, there is provided a β-lactamase inhibitor comprising the 1,1-dioxopenicillanic acid ester (I) as an active ingredient.

Furthermore, the present invention provides a pharmaceutical composition for the treatment of infectious diseases, comprising at least one 1,1-dioxopenicillanic acid ester (I) and at least one β-lactam antibiotic.

The 1,1-dioxopenicillanic acid ester (I) of this invention shows excellent β-lactamase inhibitory activity. Hence, it increases the antimicrobial activity of a β-lactam antibiotic when it is present together with the β-lactam antibiotic in vivo. It is also expected to exhibit antimicrobial activity against resistant strains.

Examples of the β-lactam antibiotics which can be used together with the ester (I) of the invention include penicillin-type antibiotics suitably used for oral administration, such as ampicillin, amoxicillin, ciclacillin, talampicillin, bacampicillin, pivmecillinam, carfecillin, and carindacillin; cephalosporin-type antibiotics used suitably for oral administration, such as cephaloglycin, cephalexin, cefadroxil, cefradine and cefatrizine; penicillin-type antibiotics suitably used for injection, such as benzylpenicillin, carbenicillin, tricarcillin, piperacillin, apalcillin, and sulbenicillin; and cephalosporin-type antibiotics suitably used for injection, such as cephalothin, cefazolin, cefoxitin, cefamandole and cephapirin.

The weight ratio of the ester (I) to the β-lactam antibiotic is usually 1:0.1–3, preferably 1:0.2–1, but is not limited to these ranges alone.

The ester (I) of this invention can be administered preferably in the following forms.

Firstly, the ester (I) of the invention and the β-lactam antibiotic are both orally administered. These compounds may be orally administered separately or simultaneously. It is especially preferred to orally administer a pharmaceutical composition for the treatment of an infectious disease containing both of these compounds.

The ester (I) of this invention and the composition mentioned above may be in various forms. For example, the two compounds, either together or individually, can be formed into powders, granules, tablets, capsules, etc. together with pharmaceutically acceptable carriers, for example diluents such as starch, lactose and crystalline cellulose, disintegrants, binders, preservatives, coating agents and lubricants.

The suitable amounts of the two compounds in these drugs can be properly determined within the proportions described hereinabove.

According to another embodiment, the ester (I) of the invention is orally administered, while the β-lactam antibiotic is administered parenterally. By orally administering the ester (I) of this invention 10 to 30 minutes before, or simultaneously with, the intravenous or intramuscular administration of the β-lactam antibiotic, the same effect as in the oral administration of the two compounds can be obtained.

The doses of the 1,1-dioxopenicillanic acid ester (I) of the invention and the β-lactam antibiotic may each be about 10 to about 200 mg/kg body weight/day when both of them are to be administered orally.

When the 1,1-dioxopenicillanic acid ester (I) of the invention is to be administered orally and the β-lactam antibiotic, as an injectable, each of them may be administered in a dose of about 10 to about 400 mg/kg body weight/day.

The following Examples illustrate the present invention more specifically.

EXAMPLE 1

Production of 1,1-dioxopenicillanic acid (5-methyl-2-oxo-1,3-dioxolen-4-yl)methyl ester (compound I-A) by method A:

(1) 4-Bromomethyl-5-methyl-1,3-dioxolen-2-one [compound of formula (III) in which R is methyl and X is bromine]

3.42 g of 4,5-dimethyl-1,3-dioxolen-2-one [compound of formula (III') in which R is methyl, prepared in accordance with the procedure described in Tetrahedron Letters, pages 1701–1704, (1972)] was dissolved in 150 ml of carbon tetrachloride. To the solution were added 5.34 g of N-bromosuccinimide and a catalytic amount of α,α'-azobisisobutyronitrile. The mixture was heated under reflux for 15 minutes. The reaction mixture was cooled with ice, and the insoluble materials were removed by filtration. The filtrate was concentrated under reduced pressure to give a syrupy residue. The residue was distilled under reduced pressure, and a fraction having a boiling point of 115° to 120° C./5 mmHg was recovered. Thus, 4.2 g (yield 73%) of the captioned compound having the following properties was obtained as a colorless liquid.

Elemental analysis for $C_5H_5BrO_3$:

|  | C | H | Br |
| --- | --- | --- | --- |
| Calculated (%) | 31.11 | 2.61 | 41.40 |
| Found (%) | 31.30 | 2.49 | 41.31 |

IR (neat) $\nu(cm^{-1})$: near 18 25 (carbonyl).
NMR ($CCl_4$) δ(ppm): 2.10 (3H, —$CH_3$, s), 4.10 (2H, —$CH_2Br$, s).

(2) 1,1-Dioxopenicillanic acid (5-methyl-2-oxo-1,3-dioxolen-4-yl)methyl ester (compound I-A)

200 mg of 1,1-dioxopenicillanic acid (II) was dissolved in 2 ml of dimethylformamide, and with ice cooling, 90 mg of potassium hydrogen carbonate and 170 mg of 4-bromomethyl-5-methyl-1,3-dioxolen-2-one were added. The mixture was stirred for 5 hours with ice cooling. To the reaction mixture were added 15 ml of ethyl acetate and 8 ml of water, and the mixture was well stirred. The ethyl acetate layer was separated, and washed successively with water and a saturated aqueous solution of sodium chloride. The ethyl acetate layer was then dried over anhydrous sodium sulfate, and concentrated under reduced pressure. The resulting syrup was treated with a mixture of ethyl acetate and ether to give 140 mg (yield 47%) of the captioned compound having the following properties as a colorless amorphous solid.

Melting point: 122°–125° C. (decomp.)
Elemental analysis for $C_{13}H_{15}O_8NS$:

|  | C | H | N |
|---|---|---|---|
| Calculated (%) | 45.21 | 4.38 | 4.06 |
| Found (%) | 45.28 | 4.65 | 3.78 |

IR (KBr) $\nu(cm^{-1})$: 1835, 1815, 1795, 1765 (carbonyl).
NMR (CDCl$_3$) $\delta$(ppm): 1.40, 1.62 (6H, CH$_3$ at the 2-position, s), 2.22

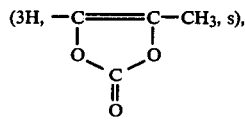

(3H, —C══C—CH$_3$, s), 3.50 (2H, proton at the 6-position, d, J=4 Hz),
4.43 (1H, proton at the 3-position, s),
4.62 (1H, proton at the 5-position, t, J=4 Hz), 4.97

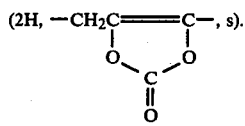

(2H, —CH$_2$C══C—, s).

The above amorphous solid [mp. 122°–125° C. (decomp.)] was recrystallized from ethyl acetate to obtain crystals of the captioned compound which had a melting point of 140° to 142° C. The product showed the same IR and NMR spectral data as above.

EXAMPLE 2

Production of 1,1-dioxopenicillanic acid (5-phenyl-2-oxo-1,3-dioxolen-4-yl)methyl ester (compound I-B) by method A:

(1) 4-Bromomethyl-5-phenyl-1,3-dioxolen-2-one [compound of formula (III) in which R is phenyl and X is bromine]

2.4 g of 5-phenyl-4-methyl-1,3-dioxolen-2-one [compound of formula (III') in which R is phenyl, prepared by the procedure described in Liebigs Annalen der Chemie, Vol. 764, pages 116–124, (1972)] was dissolved in 100 ml of carbon tetrachloride, and 2.9 g of N-bromosuccinimide and a catalytic amount of $\alpha,\alpha'$-azobisisobutyronitrile were added. The mixture was heated under reflux for 90 minutes. The reaction mixture was cooled with ice, and the insoluble materials were removed by filtration. The filtrate was concentrated under reduced pressure to give a solid. Recrystallization of the solid from a mixture of benzene and cyclohexane to give 2.3 g (yield 66%) of the captioned compound having the following properties as colorless needlelike crystals.

Melting point: 90.5°–91.5° C.
Elemental analysis for $C_{10}H_7BrO_3$:

|  | C | H | Br |
|---|---|---|---|
| Calculated (%) | 47.09 | 2.77 | 31.33 |
| Found (%) | 47.22 | 2.64 | 31.29 |

IR (KBr) $\nu(cm^{-1})$: near 1825 (carbonyl).
NMR (CCl$_4$) $\delta$(ppm): 4.35 (2H, —CH$_2$Br, s), 7.40 (5H, benzene ring, s).

(2) 1,1-Dioxopenicillanic acid (5-phenyl-2-oxo-1,3-dioxolen-4-yl)methyl ester (compound I-B)

150 mg of 1,1-dioxopenicillanic acid (II) was dissolved in 2 ml of dimethylformamide, and with ice cooling, 70 mg of potassium hydrogen carbonate and 170 mg of 4-bromomethyl-5-phenyl-1,3-dioxolen-2-one were added. With ice cooling, the mixture was stirred for 5 hours. The reaction mixture was poured into ice water, and the precipitated solid was collected by filtration. The solid was well washed with water, and dissolved in ethyl acetate. The ethyl acetate layer was washed with an aqueous solution of sodium chloride. The ethyl acetate layer was then dried over anhydrous magnesium sulfate, and concentrated under reduced pressure. The resulting syrup was crystallized from ether to give 125 mg (yield 48%) of the captioned compound having the following properties as colorless crystals.

Melting point: 100°–103° C.
Elemental analysis for $C_{18}H_{17}O_8NS$:

|  | C | H | N |
|---|---|---|---|
| Calculated (%) | 53.07 | 4.21 | 3.44 |
| Found (%) | 52.86 | 4.12 | 3.36 |

IR (KBr) $\nu(cm^{-1})$: 1845, 1830, 1795, 1760 (carbonyl).
NMR (CDCl$_3$) $\delta$(ppm): 1.44, 1.64 (6H, CH$_3$ at the 2-position, s), 3.50 (2H, proton at the 6-position, d, J=4 Hz), 4.48 (1H, proton at the 3-position, s), 4.63 (1H, proton at the 5-position, t, J=4 Hz), 5.18, 5.34

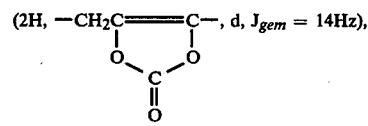

(2H, —CH$_2$C══C—, d, $J_{gem}$ = 14Hz), near 7.5 (5H, benzene ring, m).

EXAMPLE 3

Production of 1,1-dioxopenicillanic acid (5-methyl-2-oxo-1,3-dioxolen-4-yl)methyl ester (compound I-A) by method B using m-chloroperbenzoic acid:

(1) Penicillanic acid (5-methyl-2-oxo-1,3-dioxolen-4-yl)methyl ester [compound of formula (V) in which R is methyl]

2.0 g of a potassium salt of penicillanic acid (IV) was dissolved in 30 ml of dimethylformamide, and with ice cooling, 1.5 g of potassium hydrogen carbonate and 1.92 g of 4-bromomethyl-5-methyl-1,3-dioxolen-2-one obtained in Example 1, (1) were added. The mixture was stirred for 4 hours with ice cooling. To the reaction mixture was added 60 ml of ethyl acetate, and the precipitated salt was separated by filtration. The filtrate was well washed successively with water and a saturated aqueous solution of sodium chloride. The ethyl acetate layer was dried over anhydrous magnesium sulfate, and concentrated under reduced pressure to give 2.2 g (yield 84%) of the captioned compound having the following properties as a pale yellow syrup.
The syrup was directly used in the subsequent reaction.

IR (neat) $\nu(cm^{-1})$: 1830, 1780, 1760 (carbonyl).

NMR (CDCl$_3$) $\delta$(ppm): 1.45, 1.68 (6H, CH$_3$ at the 2-position, s), 2.21

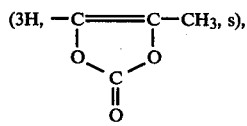
(3H, —C═══C—CH$_3$, s), 3.09 (1H, proton at the 6-position, dd, $J_{5,6}=2.0$ Hz, $J_{6,6'}=16.0$ Hz), 3.59 (1H, proton at the 6'-position, dd, $J_{5,6'}=4.0$ Hz, $J_{6,6'}=16.0$ Hz), 4.46 (1H, proton at the 3-position, s), 4.85, 4.99

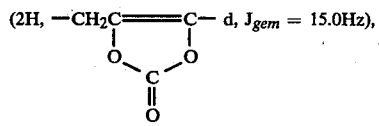
(2H, —CH$_2$C═══C— d, $J_{gem}=15.0$Hz), 5.37 (1H, proton at the 5-position, dd, $J_{5,6}=2.0$ Hz, $J_{5,6'}=4.0$ Hz).

(2) 1,1-Dioxopenicillanic acid (5-methyl-2-oxo-1,3-dioxolen-4-yl)methyl ester (compound I-A)

1.5 g of penicillanic acid (5-methyl-2-oxo-1,3-dioxolen-4-yl)methyl ester obtained in (1) above was dissolved in 10 ml of methylene chloride, and with ice cooling, a solution of 1.98 g of m-chloroperbenzoic acid in 15 ml of ethyl acetate was added dropwise. The mixture was then stirred at room temperature for 15 hours.

The reaction mixture was filtered to remove insoluble materials. The filtrate was concentrated under reduced pressure, and the resulting residue was dissolved in 40 ml of ethyl acetate. Water (30 ml) was added, and with vigorous stirring under ice cooling, the pH of the solution was adjusted to 7.8 with a 4 N aqueous solution of sodium hydroxide. Then, the ethyl acetate layer was separated, washed well with a saturated aqueous solution of sodium chloride, dried over anhydrous magnesium sulfate, and concentrated under reduced pressure. The resulting syrup was dissolved in chloroform, and ether was added. Thus, 0.65 g (yield 39.3%) of the captioned compound was obtained as a colorless solid which had the same properties as the compound obtained in Example 1, (2).

EXAMPLE 4

Production of 1,1-dioxopenicillanic acid (5-methyl-2-oxo-1,3-dioxolen-4-yl)methyl ester (compound I-A) by method B using hydrogen peroxide:

0.9 g of penicillanic acid (5-methyl-2-oxo-1,3-dioxolen-4-yl)methyl ester obtained by the same method as in Example 3, (1) was dissolved in 10 ml of tetrahydrofuran. To the solution were added 1.0 ml of 30% hydrogen peroxide and 70 mg of sodium tungstate dihydrate with ice cooling. The mixture was stirred at room temperature for 48 hours. The reaction mixture was concentrated under reduced pressure, and the residue was dissolved in 30 ml of ethyl acetate, washed successively with water and a saturated aqueous solution of sodium chloride, dried over anhydrous magnesium sulfate and concentrated under reduced pressure. The resulting syrup was dissolved in chloroform, and ether was added. Thus, 0.75 g (yield 75.5%) of the captioned compound was obtained as a colorless solid which had the same properties as the compound obtained in Example 1, (2).

EXAMPLE 5

Production of 1,1-dioxopenicillanic acid (5-phenyl-2-oxo-1,3-dioxolen-4-yl)methyl ester (compound I-B) by method B using m-chloroperbenzoic acid:

(1) Penicillanic acid (5-phenyl-2-oxo-1,3-dioxolen-4-yl)methyl ester [compound of formula (V) in which R is phenyl]

2.0 g of a potassium salt of penicillanic acid (IV) was dissolved in 20 ml of dimethylformamide, and with ice cooling, 0.8 g of potassium hydrogen carbonate and 2.1 g of 4-bromomethyl-5-phenyl-1,3-dioxolen-2-one obtained as in Example 2, (1) were added. The mixture was stirred for 4 hours with ice cooling. To the reaction mixture was added 40 ml of ethyl acetate. The mixture was filtered to remove insoluble materials, and the filtrate was washed well successively with water and a saturated aqueous solution of sodium chloride. The ethyl acetate layer was dried over anhydrous magnesium sulfate, and concentrated under reduced pressure. The resulting syrup was crystallized from a mixture of ether and n-hexane to give 2.1 g (yield 66%) of the captioned compound having the following properties as colorless needlelike crystals.

Melting point: 67°–69° C.

IR (KBr) $\nu(cm^{-1})$: 1830, 1775, 1760 (carbonyl).

NMR (CDCl$_3$) $\delta$(ppm): 1.48, 1.66 (6H, CH$_3$ at the 2-position, s), 3.04 (1H, proton at the 6-position, dd, $J_{5,6}=20$ Hz, $J_{6,6'}=16.0$ Hz), 3.54 (1H, proton at the 6'-position, dd, $J_{5,6'}=4.0$ Hz, $J_{6,6'}=16.0$ Hz), 4.51 (1H, proton at the 3-position, s), 5.10, 5.26

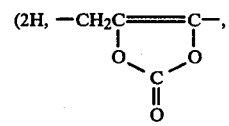
(2H, —CH$_2$C═══C—, d, $J_{gem}=15.0$ Hz), 5.25 (1H, proton at the 5-position, dd, $J_{5,6}=2.0$ Hz, $J_{5,6'}=4.0$ Hz), 7.36–7.60

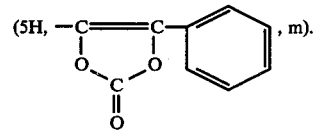
(5H, —C═══C—〔phenyl〕, m).

(2) 1,1-Dioxopenicillanic acid (5-phenyl-2-oxo-1,3-dioxolen-4-yl)methyl ester (compound I-B)

In the same way as in Example 3, (2), 2.0 g of penicillanic acid (5-phenyl-2-oxo-1,3-dioxolen-4-yl)methyl ester was oxidized with 1.84 g of m-chloroperbenzoic acid to give 0.89 g (yield 41%) of the captioned compound having the same properties as the compound obtained in Example 2, (2).

EXAMPLE 6

1,1-Dioxopenicillanic acid (5-phenyl-2-oxo-1,3-dioxolen-4-yl)methyl ester (compound I-B) by method B using hydrogen peroxide:

In the same way as in Example 4, 2.0 g of penicillanic acid (5-phenyl-2-oxo-1,3-dioxolen-4-yl)methyl ester was oxidized with 2.0 ml of 30% hydrogen peroxide and 150 mg of sodium tungstate dihydrate to give 1.65 g (yield 76%) of the captioned compound as colorless crystals. This compound had the same properties as the compound obtained in Example 2, (2).

EXAMPLE 7

Tablets comprising 1,1-dioxopenicillanic acid (5-methyl-2-oxo-1,3-dioxolen-4-yl)methyl ester (compound I-A) and ampicillin:

| | | |
|---|---|---|
| Ampicillin trihydrate | | 250 mg |
| Compound I-A | | 125 mg |
| Hydroxypropyl cellulose | | 10 mg |
| Corn starch | | 75 mg |
| Magnesium stearate | | 5 mg |
| | Total | 465 mg |

Ampicillin trihydrate, compound I-A and corn starch were mixed. The mixture was then kneaded with an aqueous solution of hydroxypropyl cellulose to prepare granules in a customary manner. The granules were mixed with magnesium stearate and tableted in a customary manner.

EXAMPLE 8

Granules comprising 1,1-dioxopenicillanic acid (5-phenyl-2-oxo-1,3-dioxolen-4-yl)methyl ester (compound I-B) and amoxicillin:

| | | |
|---|---|---|
| Amoxicillin | | 250 mg |
| Compound I-B | | 125 mg |
| Hydroxypropyl cellulose | | 20 mg |
| Crystalline cellulose | | 50 mg |
| Lactose | | 400 mg |
| Corn starch | | 155 mg |
| | Total | 1000 mg |

Amoxicillin, compound I-B, crystalline cellulose, lactose, and corn starch were mixed. The mixture was kneaded with an aqueous solution of hydroxypropyl cellulose, and formed into granules by means of an extrusion granulator.

EXAMPLE 9

Tablets comprising 1,1-dioxopenicillanic acid (5-methyl-2-oxo-1,3-dioxolen-4-yl)methyl ester (compound I-A):

| | | |
|---|---|---|
| Compound I-A | | 125 mg |
| Hydroxypropyl cellulose | | 4 mg |
| Corn starch | | 25 mg |
| Magnesium stearate | | 2 mg |
| | Total | 156 mg |

Tablets were prepared from the above ingredients in the same way as in Example 7.

What we claim:

1. A 1,1-dioxopenicillanic acid ester represented by the following formula (I)

[Structural formula (I)]

wherein R represents a methyl or phenyl group.

2. The 1,1-dioxopenicillanic acid ester of claim 1 wherein R in formula (I) is a methyl group.

3. The 1,1-dioxopenicillanic acid ester of claim 1 wherein R in formula (I) is a phenyl group.

4. A β-lactamase inhibitor composition comprising as an active ingredient a β-lactamase inhibitory amount of a 1,1-dioxopenicillanic acid ester represented by the following formula (I)

[Structural formula (I)]

wherein R represents a methyl or phenyl group in association with a pharmaceutically acceptable carrier.

5. An antibacterial composition comprising (A) a β-lactamase inhibitory amount of a 1,1-dioxopenicillanic acid ester represented by the following formula (I)

[Structural formula (I)]

wherein R represents a methyl or phenyl group, and (B) an antibacterially effective amount of a β-lactam antibiotic.

6. A composition according to claim 5, wherein the weight ratio of (A) to (B) is 1:0.1 to 1:3.

* * * * *